United States Patent
Jiang et al.

(10) Patent No.: US 10,722,612 B2
(45) Date of Patent: Jul. 28, 2020

(54) SOFT HYDROPHOBIC ACRYLIC MATERIALS

(71) Applicant: Novartis AG, Basel (CH)

(72) Inventors: Xuwei Jiang, Arlington, TX (US); Douglas Schlueter, Azle, TX (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 14/557,676

(22) Filed: Dec. 2, 2014

(65) Prior Publication Data

US 2015/0151021 A1    Jun. 4, 2015

Related U.S. Application Data

(60) Provisional application No. 61/911,549, filed on Dec. 4, 2013.

(51) Int. Cl.
| | |
|---|---|
| *C08F 220/18* | (2006.01) |
| *C08F 220/24* | (2006.01) |
| *A61L 27/16* | (2006.01) |
| *A61F 2/16* | (2006.01) |
| *G02B 1/04* | (2006.01) |
| *C08F 222/10* | (2006.01) |

(52) U.S. Cl.
CPC ............ *A61L 27/16* (2013.01); *A61F 2/1624* (2013.01); *C08F 220/24* (2013.01); *C08F 222/1006* (2013.01); *G02B 1/043* (2013.01); *C08F 220/18* (2013.01); *C08F 222/10* (2013.01)

(58) Field of Classification Search
CPC . C08F 220/24; C08F 220/18; C08F 222/1006
See application file for complete search history.

(56) References Cited

U.S. PATENT DOCUMENTS

| | | | |
|---|---|---|---|
| 3,162,676 A | 12/1964 | Goldberg | |
| 3,299,173 A | 1/1967 | Roselli | |
| 4,304,895 A | 12/1981 | Loshaek | |
| 4,528,311 A | 7/1985 | Beard | |
| 4,612,358 A | 9/1986 | Besecke | |
| 4,716,234 A | 12/1987 | Dunks | |
| 4,737,556 A | 4/1988 | Itoh | |
| 4,742,140 A * | 5/1988 | Greenwood | C08F 220/22 526/245 |
| 4,786,658 A * | 11/1988 | Hashimoto | C03C 25/105 385/145 |
| 4,787,903 A | 11/1988 | Grendahl | |
| 4,795,793 A * | 1/1989 | Amimoto | C08F 220/24 524/501 |
| 4,816,031 A | 3/1989 | Pfoff | |
| 4,932,966 A | 6/1990 | Christie | |
| 5,066,301 A | 11/1991 | Wiley | |
| 5,443,506 A | 8/1995 | Garabet | |
| 5,470,932 A | 11/1995 | Jinkerson | |
| 6,117,171 A | 9/2000 | Skottun | |
| 6,730,123 B1 | 5/2004 | Klopotek | |
| 7,122,053 B2 | 10/2006 | Esch | |
| 7,217,288 B2 | 5/2007 | Esch | |
| 7,247,168 B2 | 7/2007 | Esch | |
| 7,261,737 B2 | 8/2007 | Esch | |
| 7,438,723 B2 | 10/2008 | Esch | |
| 7,485,144 B2 | 2/2009 | Esch | |
| 7,585,900 B2 | 9/2009 | Cordova | |
| 7,605,190 B2 | 10/2009 | Moszner | |
| 7,714,039 B2 | 5/2010 | Cordova | |
| 7,753,953 B1 | 7/2010 | Yee | |
| 7,776,088 B2 | 8/2010 | Shadduck | |
| 8,034,106 B2 | 10/2011 | Mentak | |
| 8,038,711 B2 | 10/2011 | Clarke | |
| 8,048,155 B2 | 11/2011 | Shadduck | |
| 8,153,703 B2 | 4/2012 | Laredo | |
| 8,158,712 B2 | 4/2012 | Your | |
| 8,197,541 B2 | 6/2012 | Schedler | |
| 8,232,326 B2 | 7/2012 | Laredo | |
| 8,254,034 B1 | 8/2012 | Shields | |
| 8,361,145 B2 | 1/2013 | Scholl | |
| 8,398,709 B2 | 3/2013 | Ben Nun | |
| 8,454,688 B2 | 6/2013 | Esch | |
| 8,475,529 B2 | 7/2013 | Clarke | |
| 2006/0004163 A1 | 1/2006 | Makker | |
| 2008/0200982 A1 | 8/2008 | Your | |
| 2011/0188261 A1 * | 8/2011 | Deng | B29D 11/00663 362/551 |
| 2011/0306713 A1 * | 12/2011 | Ueda | C08F 2/04 524/265 |
| 2013/0268070 A1 | 10/2013 | Esch | |

FOREIGN PATENT DOCUMENTS

| | | |
|---|---|---|
| CN | 101214392 A | 7/2008 |
| CN | 101475507 A | 7/2009 |
| CN | 101564551 A | 10/2009 |
| CN | 101845114 A | 9/2010 |
| CN | 103013208 A | 4/2013 |
| CN | 103232567 A | 8/2013 |
| EP | 0461604 A2 | 12/1991 |
| EP | 1750157 A1 | 2/2007 |
| JP | S60200223 A | 10/1985 |
| JP | H0329918 A | 2/1991 |
| JP | 03140918 A | 6/1991 |
| JP | 2001066557 A | 3/2001 |

OTHER PUBLICATIONS

PCT International Search Report dated Jan. 26, 2015, International Application No. PCT/US2014/068052, International Filing Date Dec. 2, 2014.

PCT Written Opinion of the International Searching Authority dated Jan. 26, 2015, International Application No. PCT/US2014/068052, International Filing Date Dec. 2, 2014.

(Continued)

*Primary Examiner* — Karuna P Reddy
(74) *Attorney, Agent, or Firm* — Jian Zhou

(57) ABSTRACT

Soft hydrophobic acrylic materials with improved resistance to fluid diffusion and suitable mechanical properties that allow deformation upon application of force are disclosed. The acrylic materials are particularly suitable for use in fluid-based accommodating intraocular lenses and comprises combination of a perfluoro-substituted alkyl (meth)acrylate and an alkyl (meth)acrylate, and a cross-linking agent.

9 Claims, No Drawings

(56) References Cited

OTHER PUBLICATIONS

Authors: Shiro Kobayashi, Eiji Masuda, Shin-Ichiro Shoda, and Yasuo Shimano Title: Synthesis of Acryl- and Methacryl-Type Macromonomers and Telechelics by Utilizing Living Polymerization of 2-Oxazolines Published: Macromolecules (1989), vol. 22, pp. 2878-2884.

Authors: Jun Liu and Cai-Yuan Pan Title: Synthesis and characterization of H-shaped copolymers of RAFT polymerization and CROP Published: Polymer (2005) vol. 46, pp. 11133-11141.

Authors: Veerle Coessens, Yoshiki Nakagawa, Krzysztof Matyjaszewski Title: Synthesis of azido end-functionalized polyacrylates via atom transfer radical polymerization Published: Polymer Bulletin (1998) vol. 40, pp. 135-142.

\* cited by examiner

SOFT HYDROPHOBIC ACRYLIC MATERIALS

This application claims the benefits under 35 USC § 119 (e) of U.S. provisional application No. 61/911,549 filed Dec. 4, 2013, incorporated by reference in its entirety.

This invention relates generally to soft hydrophobic acrylic materials having improved resistance to fluid diffusion and suitable mechanical properties that allow deformation upon application of force, which are desirable as biocompatible materials for fluid-based accommodating intraocular lenses (IOLs).

BACKGROUND OF THE INVENTION

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

In the natural lens, bifocality of distance and near vision is provided by a mechanism known as accommodation. The natural lens is contained within the capsular bag and is soft early in life. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In this way, the natural lens can focus alternatively on near and far objects.

As the lens ages, it becomes harder and is less able to change its shape in reaction to the tightening of the ciliary muscle. This makes it harder for the lens to focus on near objects, a medical condition known as presbyopia. Presbyopia affects nearly all adults over the age of 45 or 50.

When age or disease causes the crystalline lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and ultrasonically vibrated. The vibrating cutting tip liquifies or emulsifies the lens so that the lens may be aspirated out of the eye. The diseased lens, once removed, is replaced by an artificial lens. Implantation of conventional IOLs may restore vision in cataract patients, but cannot alleviate presbyopia.

Extensive research efforts have been contributed to develop accommodating IOLs which could have the capability to either change its optical power as the natural crystalline lens in response to contraction of the cilliary muscle. One of the active research areas for accommodating IOLs is fluid-based accommodating IOLs that can undergo curvature change upon contraction/relaxation of cilliary muscle (e.g., U.S. Pat. Nos. 4,787,903, 4,816,031, 4,932,966, 5,066,301, 5,443,506, 6,117,171, 6,730,123, 7,122,053, 7,217,288, 7,247,168, 7,261,737, 7,438,723, 7,485,144, 7,753,953, 7,776,088, 8,038,711, 8,048,155, 8,158,712, 8,197,541, 8,361,145, 8,398,709, 8,454,688, 8,475,529, and U.S. patent application publication No. 2013/02668070 A1, herein incorporated by reference in their entireties). U.S. Pat. No. 8,158,712 described biocompatible polymers which comprise trifluoroethyl methacrylate (or its alternative), butyl acrylate (or its alternative), and phenyl ethylacrylate (or its alternative), and have a modulus of elasticity between about 0.1 MPa and about 0.6 MPa and a refractive index between about 1.44 and about 1.52, and is substantially resistant to the diffusion of fluid, such as silicone oil, water or saline. According to U.S. Pat. No. 8,158,712, those biocompatible polymers may be useful for making accommodating IOLs, which comprise a deformable optics front surfaces and soft deformable haptics that rely on fluid driving changes in the shape of the deformable optics's front surface.

SUMMARY

Soft hydrophobic acrylic materials which are particularly suited for use as fluid-based accommodating IOLs, but which are also useful as other ophthalmic or otorhinolaryngological devices, such as contact lenses, keratoprostheses, corneal rings or inlays, otological ventilation tubes and nasal implants, have been discovered. These polymeric materials comprise a selected combination of a perfluoro acrylic monomer and a hydrocarbon acrylic monomer.

Among other factors, the present invention is based on the finding that proper combination of perfluoro acrylic monomers and hydrocarbon acrylic monomers results in soft hydrophobic materials that showed desirable mechanical properties, (e.g., a storage modulus of from about 1 MPa to about 3 MPa) and very low silicone uptake after accelerated aging in high refractive index silicone oil. The subject materials are particularly suitable for making fluid-based accommodating IOLs.

DETAILED DESCRIPTION OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

"About" as used herein means that a number referred to as "about" comprises the recited number plus or minus 1-10% of that recited number.

"Optional" or "optionally" means that the subsequently described event or circumstance can or cannot occur, and that the description includes instances where the event or circumstance occurs and instances where it does not.

Unless indicated otherwise, all component amounts are presented on a % (w/w) basis ("wt. %").

The term "alkyl" refers to a monovalent radical obtained by removing a hydrogen atom from a linear or branched alkane compound. An alkyl group (radical) forms one bond with one other group in an organic compound.

The term "perfluoro-substituted alkyl" refers to an alkyl radical comprising at least three fluorine atoms each of which replaces one hydrogen atom of the alkyl.

The term "alkylene divalent group" or "alkylene diradical" or "alkyl diradical" interchangeably refers to a divalent radical obtained by removing one hydrogen atom from an alkyl. An alkylene divalent group forms two bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

In this application, the term "substituted" in reference to an alkyl diradical or an alkyl radical means that the alkyl diradical or the alkyl radical comprises at least one substituent which replaces one hydrogen atom of the alkyl diradical or the alkyl radical and is selected from the group consisting of hydroxy (—OH), carboxy (—COOH), —NH$_2$, sulfhydryl (—SH), C$_1$-C$_4$ alkyl, C$_1$-C$_4$ alkoxy, C$_1$-C$_4$ alkylthio (alkyl sulfide), C$_1$-C$_4$ acylamino, C$_1$-C$_4$ alkylamino, di-C$_1$-C$_4$ alkylamino, halogen atom (Br or Cl), and combinations thereof.

The term "(meth)acrylate" refers to a monomer containing a radical of —O—C(═O)—CH═CH$_2$ or —O—C(═O)—C(CH$_3$)═CH$_2$.

The term "aryl acrylic monomer" refers to a monomer of the following formula

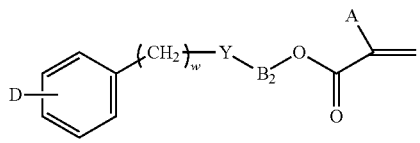

wherein: A is H or CH$_3$; B$_2$ is (CH$_2$)$_m$ or [O(CH$_2$)$_2$]$_z$; m is 2-6; z is 1-10; Y is a direct bond, O, S, or NR', provided that if Y is O, S, or NR', then B is (CH$_2$)$_m$; R' is H, CH$_3$, C$_n$H$_{2n'+1}$, iso-OC$_3$H$_7$, C$_6$H$_5$, or CH$_2$C$_6$H$_5$; n'=1-10; w is 0-6, provided that m+w≥8; and D is H, Cl, Br, C$_1$-C$_4$ alkyl, C$_1$-C$_4$ alkoxy, C$_6$H$_5$, or CH$_2$C$_6$H$_5$. Examples of aryl acrylic monomers include, but are not limited to: 2-ethylphenoxy acrylate; 2-ethylphenoxy methacrylate; phenyl acrylate; phenyl methacrylate; benzyl acrylate; benzyl methacrylate; 2-phenylethyl acrylate; 2-phenylethyl methacrylate; 3-phenylpropyl acrylate; 3-phenylpropyl methacrylate; 4-phenylbutyl acrylate; 4-phenylbutyl methacrylate; 4-methylphenyl acrylate; 4-methylphenyl methacrylate; 4-methylbenzyl acrylate; 4-methylbenzyl methacrylate; 2-2-methylphenylethyl acrylate; 2,2-methylphenylethyl methacrylate; 2,3-methylphenylethyl acrylate; 2,3-methylphenylethyl methacrylate; 2,4-methylphenylethyl acrylate; 2,4-methylphenylethyl methacrylate; 2-(4-propylphenyl)ethyl acrylate; 2-(4-propylphenyl)ethyl methacrylate; 2-(4-(1-methylethyl)phenyl)ethyl acrylate; 2-(4-(1-methylethyl)phenyl)ethyl methacrylate; 2-(4-methoxyphenyl)ethyl acrylate; 2-(4-methoxyphenyl)ethyl methacrylate; 2-(4-cyclohexylphenyl)ethyl acrylate; 2-(4-cyclohexylphenyl)ethyl methacrylate; 2-(2-chlorophenyl)ethyl acrylate; 2-(2-chlorophenyl)ethyl methacrylate; 2-(3-chlorophenyl)ethyl acrylate; 2-(3-chlorophenyl)ethyl methacrylate; 2-(4-chlorophenyl)ethyl acrylate; 2-(4-chlorophenyl)ethyl methacrylate; 2-(4-bromophenyl)ethyl acrylate; 2-(4-bromophenyl)ethyl methacrylate; 2-(3-phenylphenyl)ethyl acrylate; 2-(3-phenylphenyl)ethyl methacrylate; 2-(4-phenylphenyl)ethyl acrylate; 2-(4-phenylphenyl)ethyl methacrylate; 2-(4-benzylphenyl)ethyl acrylate; 2-(4-benzylphenyl)ethyl methacrylate; 2-(phenylthio)ethyl acrylate; 2-(phenylthio)ethyl methacrylate; 2-benzyloxyethyl acrylate; 3-benzyloxypropyl acrylate; 2-benzyloxyethyl methacrylate; 3-benzyloxypropyl methacrylate; 2-[2-(benzyloxy)ethoxy]ethyl acrylate; 2-[2-(benzyloxy)ethoxy]ethyl methacrylate; or combinations thereof.

In general, the invention is directed to soft, hydrophobic acrylic materials having improved resistance to fluid diffusion and suitable mechanical properties that allow deformation upon application of force. A soft hydrophobic acrylic material of the invention is characterized by having a storage modulus of from about 0.5 MPa to about 3.0 MPa (preferably from about 0.75 MPa to about 2.5 MPa, more preferably from about 1.0 MPa to about 2.0 MPa) measured by dynamic mechanical analysis (DMA) under compression mode at about 35° C. and a silicone uptake of less than about 2.0% by weight (preferably less than about 1.5% by weight, more preferably less than about 1.0% by weight or less, even more preferably about 0.8% by weight or less, most preferably about 0.5% by weight or less) after accelerated aging in a silicone fluid for 32 days at 70° C., and is obtained from a polymerizable composition comprising from about 55% to about 90% by weight (preferably from about 60% to about 85% by weight, more preferably from about 65% to about 80% by weight) of at least one perfluoro-substituted-C$_2$-C$_{12}$ alkyl (meth)acrylate; from about 10% to about 45% by weight (preferably from about 15% to about 40% by weight, more preferably from about 20% to about 35% by weight) of at least one C$_2$-C$_{12}$ alkyl (meth)acrylate; and at least one cross-linking agent, provided that the polymerizable composition is substantially free (i.e., less than about 2% by weight, preferably less than about 1% by weight, more preferably about 0.5% by weight or less, even more preferably about 0.1% by weight or less, most preferably totally) of any aryl acrylic monomer.

Any suitable C$_2$-C$_{12}$ alkyl (meth)acrylates can be used in the invention. Examples of preferred C$_2$-C$_{12}$ alkyl (meth)acrylates include without limitation, ethyl acrylate, ethyl methacrylate, n-propyl acrylate, n-propyl methacrylate, n-butyl acrylate, n-butyl methacrylate, n-pentyl acrylate, n-pentyl methacrylate, n-hexyl acrylate, n-hexyl methacrylate, n-heptyl acrylate, n-heptyl methacryate, n-octyl acrylate, n-octyl methacrylate, n-nonyl acrylate, n-nonyl methacrylate, n-decyl acrylate, n-decyl methacrylate, n-undecyl acrylate, n-undecyl methacrylate, lauryl acrylate, lauryl methacrylate, 2-ethylhexyl acrylate, 2-ethylhexyl methacrylate, 2,2-dimethylpropyl acrylate, 2,2-dimethylpropyl methacrylate, trimethylcyclohexyl acrylate, trimethylcyclohexyl methacrylate, isobutyl acrylate, isobutyl methacrylate, isopentyl acrylate, isopentyl methacrylate, and mixtures thereof.

Any suitable perfluoro-substituted-C$_2$-C$_{12}$ alkyl (meth)acrylates can be used in the invention. Examples of perfluoro-substituted-C$_2$-C$_{12}$ alkyl (meth)acrylates include without limitation 2,2,2-trifluoroethyl methacrylate, 2,2,2-trifluoroethyl acrylate, tetrafluoropropyl methacrylate, tetrafluoropropyl acrylate, hexafluoro-iso-propyl methacrylate, hexafluoro-iso-propyl acrylate, hexafluorobutyl methacrylate, hexafluorobutyl acrylate, heptafluorobutyl methacrylate, heptafluorobutyl acrylate, octafluoropentyl methacrylate, octafluoropentyl acrylate, dodecafluoroheptyl methacrylate, heptadecafluorodecyl acrylate, heptadecafluorodecyl methacrylate, pentafluorophenyl acrylate, pentafluorophenyl methacrylate, and combinations thereof.

The cross-linking agent may be any terminally ethylenically unsaturated compound having more than one unsaturated groups. Suitable cross-linking agents include, for example: ethylene glycol dimethacrylate; diethylene glycol dimethacrylate; triethylene glycol dimethacrylate, tetraethylene glycol dimethacrylate, allyl methacrylate; 1,3-propanediol dimethacrylate; 2,3-propanediol dimethacrylate; 1,6-hexanediol dimethacrylate; 1,4-butanediol dimethacrylate; $CH_2=C(CH_3)C(=O)O—(CH_2CH_2O)_p—C(=O)C(CH_3)=CH_2$ where p=1-50; and $CH_2=C(CH_3)C(=O)O(CH_2)_tO—C(=O)C(CH3)=CH2$ where t=3-20; their corresponding acrylates; and combinations thereof. A preferred cross-linking monomer is $CH_2=C(CH_3)C(=O)O—(CH_2CH_2O)_p—C(=O)C—(CH_3)=CH_2$ where p is such that the number-average molecular weight is about 400, about 600, or about 1000. Other preferred cross-linking monomers are ethylene glycol dimethacrylate (EGDMA), diethylene glycol dimethacrylate, triethylene glycol dimethacrylate, triethylene glycol diacrylate, and 1,4-butanediol diacrylate (BDDA).

Generally, the total amount of the cross-linking component is at least 0.1% by weight and, depending on the identity and concentration of the remaining components and the desired physical properties of the acrylic material, can range up to about 20% by weight. The preferred concentration range for the cross-linking component is 1-5% for small compounds with molecular weights typically less than 500 Daltons, and 5-17% (w/w) for larger compounds (with molecular weights typically greater than 500 Daltons).

In addition to one or more perfluoro-substituted-$C_2$-$C_{12}$ (meth)acrylates, one or more $C_2$-$C_{12}$ alkyl (meth)acrylates, and one or more cross-linking agents, the acrylic materials of the present invention may also contain other ingredients, including, but not limited to, polymerizable UV-absorbers (or UV-absorbing agents), polymerizable colored dyes, additives to reduce tack, and combinations thereof.

A polymerizable ultraviolet (UV) absorbing agent can also be included in the materials of the present invention. The polymerizable UV-absorbing agent can be any compound which absorbs UV light (i.e., light having a wavelength shorter than about 380 nm) and optionally high-energy-violet-light (HEVL) (i.e., light having a wavelength between 380 nm and 440 nm), but does not absorb any substantial amount of visible light having a wavelength greater than 440 nm. The UV-absorbing compound is incorporated into the monomer mixture and is entrapped in the polymer matrix when the monomer mixture is polymerized. Any suitable polymerizable UV-absorbing agents can be used in the invention. A polymerizable UV-absorbing agent used in the invention comprises a benzophenone-moiety or preferably a benzotriazole-moiety. Polymerizable benzophenone-containing UV-absorbing agents can be prepared according to procedures described in U.S. Pat. Nos. 3,162,676 and 4,304,895 (herein incorporated by reference in their entirety) or can be obtained from commercial suppliers. Polymerizable benzotriazole-containing UV-absorbing agents can be prepared according to procedures described in U.S. Pat. Nos. 3,299,173, 4,612,358, 4,716,234, 4,528,311, 8,153,703, and U.S. Pat. No. 8,232,326 (herein incorporated by reference in their entireties) or can be obtained from commercial suppliers.

Examples of preferred polymerizable benzophenone-containing UV-absorbing agents include without limitation 2-hydroxy-4-acryloxy alkoxy benzophenone, 2-hydroxy-4-methacryloxy alkoxy benzophenone, allyl-2-hydroxybenzophenone, 4-acryloylethoxy-2-hydroxybenzophenone (UV2), 2-hydroxy-4-methacryloyloxybenzophenone (UV7), or combinations thereof.

Examples of preferred polymerizable benzotriazole-containing UV-absorbing and UV/HEVL-absorbing agents include without limitation: 2-(2-hydroxy-5-vinylphenyl)-2H-benzotriazole, 2-(2-hydroxy-5-acrylyloxyphenyl)-2H-benzotriazole, 2-(2-hydroxy-3-methacrylamido methyl-5-tert octylphenyl) benzotriazole, 2-(2'-hydroxy-5'-methacrylamidophenyl)-5-chlorobenzotriazole, 2-(2'-hydroxy-5'-methacrylamidophenyl)-5-methoxybenzotriazole, 2-(2'-hydroxy-5'-methacryloxypropyl-3'-t-butyl-phenyl)-5-chlorobenzotriazole, 2-(2'-hydroxy-5'-methacryloxypropylphenyl) benzotriazole, 2-hydroxy-5-methoxy-3-(5-(trifluoromethyl)-2H-benzo[d] [1,2,3]triazol-2-yl)benzyl methacrylate (WL-1), 2-hydroxy-5-methoxy-3-(5-methoxy-2H-benzo[d] [1,2,3]triazol-2-yl)benzyl methacrylate (WL-5), 3-(5-fluoro-2H-benzo[d] [1,2,3]triazol-2-yl)-2-hydroxy-5-methoxybenzyl methacrylate (WL-2), 3-(2H-benzo[d] [1,2,3]triazol-2-yl)-2-hydroxy-5-methoxybenzyl methacrylate (WL-3), 3-(5-chloro-2H-benzo[d] [1,2,3]triazol-2-yl)-2-hydroxy-5-methoxybenzyl methacrylate (WL-4), 2-hydroxy-5-methoxy-3-(5-methyl-2H-benzo[d] [1,2,3]triazol-2-yl)benzyl methacrylate (WL-6), 2-hydroxy-5-methyl-3-(5-(trifluoromethyl)-2H-benzo[d] [1,2,3]triazol-2-yl)benzyl methacrylate (WL-7), 4-allyl-2-(5-chloro-2H-benzo[d] [1,2,3]triazol-2-yl)-6-methoxyphenol (WL-8), 2-{2'-Hydroxy-3'-tert-5' [3"-(4"-vinylbenzyloxy)propoxy]phenyl}-5-methoxy-2H-benzotriazole, phenol, 2-(5-chloro-2H-benzotriazol-2-yl)-6-(1,1-dimethylethyl)-4-ethenyl-(UVAM), 2-(2'-hydroxy-5'-methacryloxyethylphenyl) benzotriazole (2-Propenoic acid, 2-methyl-, 2-[3-(2H-benzotriazol-2-yl)-4-hydroxyphenyl] ethyl ester, Norbloc), 2-{2'-Hydroxy-3'-tert-butyl-5'-[3'-methacryloyloxypropoxy]phenyl}-5-methoxy-2H-benzotriazole (UV13), 2-[2'-Hydroxy-3'-tert-butyl-5'-(3'-acryloyloxypropoxy)phenyl]-5-trifluoromethyl-2H-benzotriazole ($CF_3$-UV13), 2-(2'-hydroxy-5-methacrylamidophenyl)-5-methoxybenzotriazole (UV6), 2-(3-allyl-2-hydroxy-5-methylphenyl)-2H-benzotriazole (UV9), 2-(2-Hydroxy-3-methallyl-5-methylphenyl)-2H-benzotriazole (UV12), 2-3'-t-butyl-2'-hydroxy-5'-(3"-dimethylvinylsilylpropoxy)-2'-hydroxy-phenyl)-5-methoxybenzotriazole (UV15), 2-(2'-hydroxy-5'-methacryloylpropyl-3'-tert-butyl-phenyl)-5-methoxy-2H-benzotriazole (UV16), 2-(2'-hydroxy-5'-acryloylpropyl-3'-tert-butyl-phenyl)-5-methoxy-2H-benzotriazole (UV16A), 2-Methylacrylic acid 3-[3-tert-butyl-5-(5-chlorobenzotriazol-2-yl)-4-hydroxyphenyl]-propyl ester (16-100, CAS #96478-15-8), 2-(3-(tert-butyl)-4-hydroxy-5-(5-methoxy-2H-benzo[d] [1,2,3]triazol-2-yl)phenoxy)ethyl methacrylate (16-102); Phenol, 2-(5-chloro-2H-benzotriazol-2-yl)-6-methoxy-4-(2-propen-1-yl) (CAS #1260141-20-5); 2-[2-Hydroxy-5-[3-(methacryloyloxy)propyl]-3-tert-butylphenyl]-5-chloro-2H-benzotriazole; Phenol, 2-(5-ethenyl-2H-benzotriazol-2-yl)-4-methyl-, homopolymer (9CI) (CAS #83063-87-0).

More preferably, a polymerizable UV-absorbing agent is 2-(2H-benzo[d] [1,2,3]triazol-2-yl)-4-methyl-6-(2-methylallyl)phenol (oNTP), 3-[3-tert-butyl-4-hydroxy-5-(5-methoxy-2-benz[d] [1,2,3]triazol-2-yl)phenoxy]propyl methacrylate (UV13), and 2-[3-(2H-benzotriazol-2-yl)-4-hydroxyphenyl]ethyl methacrylate (Norbloc 7966), or combinations thereof.

In addition to ultraviolet absorbing materials, the acrylic materials of the present invention may include colored dyes, such as the yellow dyes disclosed in U.S. Pat. No. 5,470,932.

The device materials of the present invention may also contain additives to reduce or eliminate tack. Examples of such additives include those disclosed in U.S. Pat. Nos. 7,585,900 and 7,714,039, the entire contents of which are incorporated by reference herein.

In a more preferred embodiment, the acrylic material of the invention comprises heptadecafluorodecyl methacrylate as the perfluoro-substituted-$C_2$-$C_{12}$ alkyl (meth)acrylate, butyl acrylate as the $C_2$-$C_{12}$ alkyl (meth)acrylate, and ethylene glycol dimethacrylate as the cross-linking agent.

The acrylic materials of this invention are prepared by conventional polymerization methods. For example, a mixture of a perfluoro-substituted-$C_2$-$C_{12}$ alkyl (meth)acrylate, a $C_2$-$C_{12}$ alkyl (meth)acrylate, a cross-linking agent in the desired proportions, and a free-radical initiator, together with any other polymerizable components (such as a polymerizable UV-absorber, polymerizable yellow dye, and/or additive to reduce tack), is prepared. The mixture can then be introduced into a mold of desired shape, and the polymerization carried out thermally (i.e., by heating) or photochemically (i.e., by actinic radiation, e.g., UV radiation and/or visible radiation) to activate the initiator.

Examples of suitable thermal initiators include: but are not limited to, azonitriles, such as 2,2'-azobis (2,4-dimethylpentanenitrile), 2,2'-azobis (2-methylpropanenitrile), 2,2'-azobis (2-methylbutanenitrile), 2,2'-azobis(isobutyronitrile) (AIBN); peroxides, such as benzoyl peroxide; peroxycarbonates, such as bis-(4-t-butylcyclohexyl) peroxydicarbonate, and the like. A preferred initiator is AIBN.

Where the polymerization is carried out photochemically, a mold should be transparent to actinic radiation of a wavelength capable of initiating polymerization. Conventional photoinitiator compounds, e.g., a benzophenone-type or bisacylphosphine oxide (BAPO) photoinitiator, can also be introduced to facilitate the polymerization. Suitable photoinitiators are benzoin methyl ether, diethoxyacetophenone, a benzoylphosphine oxide, 1-hydroxycyclohexyl phenyl ketone, Darocur and Irgacur types photoinitiators (preferably Darocur 1173®, Darocur 2959® and Irgacure 819®), and Germane-based Norrish Type I photoinitiators which are capable of initiating a free-radical polymerization under irradiation with a light source including a light in the region of about 400 to about 550 nm. Examples of benzoylphosphine initiators include 2,4,6-trimethylbenzoyldiphenylophosphine oxide; bis-(2,6-dichlorobenzoyl)-4-N-propylphenylphosphine oxide; and bis-(2,6-dichlorobenzoyl)-4-N-butylphenylphosphine oxide. Examples of Germane-based Norrish Type I photoinitiators are acylgermanium compounds described in U.S. Pat. No. 7,605,190 (herein incorporated by reference in its entirety).

Regardless of the chosen initiator or curing method, the curing process should be controlled to avoid rapid polymerization, which may yield polymerized materials having more tack than the same materials polymerized more slowly.

Once the acrylic materials of the present invention have been cured, they are extracted in a suitable solvent to remove as much of the unreacted components of the materials as possible. Examples of suitable solvents include acetone, methanol, and cyclohexane. A preferred solvent for extraction is acetone.

Fluid-based accommodating IOLs constructed of the disclosed acrylic materials can be of any design capable of changing optical power as the natural crystalline lens in response to contraction of the cilliary muscle. Examples of such accommodating IOLs include without limitation those described in U.S. Pat. Nos. 8,361,145, 8,254,034, 8,034,106, and 6,730,123 (herein incorporated by references in their entireties).

In addition to IOLs, the acrylic materials of the present invention are also suitable for use in other devices, including contact lenses, keratoprostheses, intracorneal lenses, corneal inlays or rings, and glaucoma filtration devices.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

EXAMPLES

The formulation components are shown in Table 1 and Table 2. Test samples measuring 0.9 mm in thickness were photo-cured by pre-heating the formulation-filled molds in a nitrogen filled glove box for 10 minutes at 55° C. and then irradiating with a Philips TLK 40W/03 24-inch fluorescent lamp for 60 minutes. Cured samples were continuously extracted in acetone for 3 days and then dried slowly at ambient temperature for 20 hours, followed by vacuum (0.1 mm Hg) for a minimum of 20 hours at 70° C. The weight of each sample was then recorded and each sample was placed into a 5 mL glass vial containing 5.0 g of poly(phenylmethylsiloxane) [Mn: ~2600, free of low molecular weight fraction (<1000))]. Steps were taken to make sure the sample was completely submerged in the liquid. The vial was then sealed with PTFE-faced butyl stopper and placed into a 70° C. convection oven. Samples were removed from the oven at pre-determined time intervals, carefully wiped with Kimwipes to removal any residual silicone fluid on the surface, and weighed.

TABLE 1

| Component | EXAMPLE IDs (% w/w) | | | | |
|---|---|---|---|---|---|
|  | 32A | 32B | 32C | 32D | 45B |
| BA | 44.65 | 53.82 | 44.64 | 54.03 | 47.00 |
| TFEMA | 23.47 | 23.59 | — | — | — |
| PEA | 30.83 | 20.99 | 30.83 | 20.73 | — |
| HFIPA | — | — | 23.48 | 23.66 | — |
| HFBMA | — | — | — | — | 50.00 |
| EGDMA | 1.05 | 1.60 | 1.05 | 1.58 | 3.00 |
| Irgacure 819 | 0.30 | 0.30 | 0.30 | 0.30 | 0.31 |

TABLE 2

| Component | EXAMPLE IDs (% w/w) | | | | |
|---|---|---|---|---|---|
|  | 36E | 36F | 36G | 36H | 36I |
| HFMA | 65.00 | 50.02 | 34.99 | 65.01 | 65.01 |
| BA | 32.00 | 46.49 | 61.01 | 32.99 | 34.00 |
| EGDMA | 3.00 | 3.50 | 4.00 | 2.00 | 1.00 |
| Irgacure 819 | 0.30 | 0.30 | 0.30 | 0.30 | 0.30 |

BA=n-butyl acrylate

TFEMA=2,2,2-trifluoroethyl methacrylate

PEA=2-phenylethyl acrylate

HFIPA=1,1,1,3,3,3-hexafluoroisopropyl acrylate

HFBMA=2,2,3,3,4,4,4-heptafluorobutyl methacrylate

EGDMA=ethylene glycol dimethacrylate

Irgacure 819=phenylbis(2,4,6-trimethylbenzoyl)phosphine oxide

HFMA=1H, 1H,2H2H-heptadecafluorodecyl methacrylate

Weight percent extractables, mechanical properties, and weight percent silicone uptakes are shown in Table 3.

TABLE 3

| Sample ID | % Extractables (N ≥ 8) | Storage Modulus at 35° C. (MPa) | % silicone uptake after 28 days in silicone oil at 70° C. | % silicone uptake after 32 days in silicone oil at 70° C. |
|---|---|---|---|---|
| 32A | 4.1 ± 0.2 | 0.55 ± 0.02 | 11.7 ± 0.3 | — |
| 32B | 3.0 ± 0.1 | 0.71 ± 0.02 | 15.4 ± 0.2 | — |
| 32C | 8.2 ± 0.5 | 0.32 ± 0.02 | 16.4 ± 0.4 | — |
| 32D | 7.0 ± 0.2 | 0.42 ± 0.02 | 26.4 ± 2.6 | — |
| 45B | 2.5 ± 0.1 | 1.61 ± 0.08 | — | 0.88 ± 0.08 |
| 36E | 3.3 ± 0.1 | 2.07 ± 0.08 | — | 0.24 ± 0.02 |
| 36F | 4.0 ± 0.1 | 1.28 ± 0.03 | — | 2.68 ± 0.29 |
| 36G | 4.1 ± 0.1 | 1.23 ± 0.08 | — | 13.11 ± 0.50 |
| 36H | 3.8 ± 0.1 | — | — | 0.46 ± 0.06 |
| 36I | 4.9 ± 0.3 | — | — | 0.86 ± 0.07 |

We claim:

1. A soft hydrophobic acrylic material,
being characterized by having a storage modulus of from about 0.5 MPa to about 3.0 MPa measured by dynamic mechanical analysis under compression mode at about 35° C. and a silicone uptake of less than about 2.0% by weight after accelerated aging in a silicone fluid for 32 days at 70° C.,
wherein the acrylic material is obtained from a polymerizable composition comprising:
a) from about 65% to about 80% by weight of at least one perfluoro-substitued-$C_2$-$C_{12}$ alkyl (meth)acrylate which is selected from the group consisting of 2,2,2-trifluoroethyl methacrylate, 2,2,2-trifluoroethyl acrylate, tetrafluoropropyl methacrylate, tetrafluoropropyl acrylate, hexafluoroisopropyl methacrylate, hexafluoroisopropyl acrylate, hexafluorobutyl methacrylate, hexafluorobutyl acrylate, heptafluorobutyl methacrylate, heptafluorobutyl acrylate, octafluoropentyl methacrylate, octafluoropentyl acrylate, dodecafluoroheptyl methacrylate, heptadecafluorodecyl acrylate, heptadecafluorodecyl methacrylate, and combinations thereof;
b) from about 20% to about 35% by weight of at least one $C_2$-$C_{12}$ alkyl (meth)acrylate which is selected from the group consisting of ethyl acrylate, ethyl methacrylate, n-propyl acrylate, n-propyl methacrylate, n-butyl acrylate, n-butyl methacrylate, n-pentyl acrylate, n-pentyl methacrylate, n-hexyl acrylate, n-hexyl methacrylate, n-heptyl acrylate, n-heptyl methacryate, n-octyl acrylate, n-octyl methacrylate, n-nonyl acrylate, n-nonyl methacrylate, n-decyl acrylate, n-decyl methacrylate, n-undecyl acrylate, n-undecyl methacrylate, lauryl acrylate, lauryl methacrylate, 2-ethylhexyl acrylate, 2-ethylhexyl methacrylate, 2,2-dimethylpropyl acrylate, 2,2-dimethylpropyl methacrylate, isobutyl acrylate, isobutyl methacrylate, isopentyl acrylate, isopentyl methacrylate, and mixtures thereof; and
c) at least one cross-linking agent which is selected from the group consisting of ethylene glycol dimethacrylate, diethylene glycol dimethacrylate, triethylene glycol dimethacrylate, tetraethylene glycol dimethacrylate, allyl methacrylate, 1,3-propanediol dimethacrylate, 2,3-propanediol dimethacrylate, 1,6-hexanediol dimethacrylate, 1,4-butanediol dimethacrylate, their corresponding acrylates, and combinations thereof, provided that the polymerizable composition is substantially free of any aryl acrylic monomer.

2. The acrylic material of claim 1, wherein the acrylic material is characterized by having a storage modulus of from about 0.75 MPa to about 2.5 MPa measured by dynamic mechanical analysis under compression mode at about 35° C. and a silicone uptake of less than about 1.5% by weight after accelerated aging in a silicone fluid for 32 days at 70° C.

3. The acrylic material of claim 1, wherein the acrylic material is characterized by having a storage modulus of from about 1.0 MPa to about 2.0 MPa measured by dynamic mechanical analysis under compression mode at about 35° C. and a silicone uptake of less than about 1.0% by weight or less after accelerated aging in a silicone fluid for 32 days at 70° C.

4. The acrylic material of claim 1, wherein said at least one $C_2$-$C_{12}$ alkyl (meth)acrylate is selected from the group consisting of n-butyl acrylate, n-butyl methacrylate, and mixtures thereof.

5. The acrylic material of claim 4, wherein said at least one cross-linking agent is selected from the group consisting of: ethylene glycol dimethacrylate; diethylene glycol dimethacrylate; triethylene glycol dimethacrylate, 1,4-butanediol dimethacrylate; their corresponding acrylates; and combinations thereof.

6. The acrylic material of claim 1, wherein polymerizable composition comprises heptadecafluorodecyl methacrylate, butyl acrylate, and ethylene glycol dimethacrylate.

7. The acrylic material of claim 2, wherein said at least one $C_2$-$C_{12}$ alkyl (meth)acrylate is selected from the group consisting of n-butyl acrylate, n-butyl methacrylate, and mixtures thereof.

8. The acrylic material of claim 7, wherein said at least one cross-linking agent is selected from the group consisting of: ethylene glycol dimethacrylate; diethylene glycol dimethacrylate; triethylene glycol dimethacrylate, 1,4-butanediol dimethacrylate; their corresponding acrylates; and combinations thereof.

9. The acrylic material of claim 2, wherein polymerizable composition comprises heptadecafluorodecyl methacrylate, butyl acrylate, and ethylene glycol dimethacrylate.

* * * * *

UNITED STATES PATENT AND TRADEMARK OFFICE
CERTIFICATE OF CORRECTION

PATENT NO. : 10,722,612 B2
APPLICATION NO. : 14/557676
DATED : July 28, 2020
INVENTOR(S) : Jiang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 506 days.

Signed and Sealed this
Twenty-sixth Day of April, 2022

*Katherine Kelly Vidal*

Katherine Kelly Vidal
*Director of the United States Patent and Trademark Office*